(12) United States Patent
Johnsson et al.

(10) Patent No.: US 12,324,762 B2
(45) Date of Patent: Jun. 10, 2025

(54) ANKLE/FOOT ORTHOSIS

(71) Applicant: OTTOBOCK SE & CO. KGAA, Duderstadt (DE)

(72) Inventors: Jan Johnsson, Norrkoping (SE); Gordon Siewert, Gottingen (DE); Heiko Drewitz, Gleichen (DE); Olaf Kroll-Orywahl, Gottingen (DE); Maximilian Segl, Duderstadt (DE); Marcus Lurssen, Gottingen (DE); Markus Tuttemann, Duderstadt (DE); Boris Ljubimir, Waltrop (DE); Norbert Schimek, Duderstadt (DE); Wolfgang Keiner, Kirchworbis (DE); Alexander Schmitt, Kassel (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 0 days.

(21) Appl. No.: 18/539,596

(22) Filed: Dec. 14, 2023

(65) Prior Publication Data

US 2024/0108490 A1    Apr. 4, 2024

Related U.S. Application Data

(63) Continuation of application No. 18/074,258, filed on Dec. 2, 2022, now Pat. No. 11,850,177, which is a
(Continued)

(30) Foreign Application Priority Data

Jun. 12, 2012   (DE) .......................... 102012011466.4

(51) Int. Cl.
*A61F 5/00*    (2006.01)
*A61F 5/01*    (2006.01)

(52) U.S. Cl.
CPC .......... *A61F 5/0127* (2013.01); *A61F 5/0111* (2013.01)

(58) Field of Classification Search
CPC .... A61F 5/0127; A61F 5/0111; A61F 5/0113; A61F 5/0123; A61F 5/0104;
(Continued)

(56) References Cited

U.S. PATENT DOCUMENTS 2,440,894 A * 5/1948 Caesar .................. A61F 5/0113
602/29
2,949,111 A * 8/1960 Ruotoistenmaki .... A61F 5/0113
602/28

(Continued)

FOREIGN PATENT DOCUMENTS

CN    101115452 A    1/2008
CN    201445580 U    5/2010
(Continued)

OTHER PUBLICATIONS

"International Search Report and Written Opinion of the International Searching Authority," issued in connection with Int'l Appl. No. PCT/EP2013/001663, dated Aug. 20, 2013 (20 pages).

*Primary Examiner* — Adam Baker
(74) *Attorney, Agent, or Firm* — HOLLAND & HART LLP

(57) ABSTRACT

An ankle/foot orthosis with a foot part, which has a sole for receiving a foot, and with a shin part which, when fitted in place, bears on the frontal aspect of a shin and is connected to the foot part via a medially extending spring, wherein the spring, behind an ankle area, forms a hinge area that allows a movement of the shin part relative to the foot part in the anterior-posterior direction.

21 Claims, 2 Drawing Sheets

Related U.S. Application Data continuation of application No. 16/926,595, filed on Jul. 10, 2020, now Pat. No. 11,517,463, which is a continuation of application No. 14/406,835, filed as application No. PCT/EP2013/001663 on Jun. 6, 2013, now Pat. No. 10,729,574.

(58) Field of Classification Search
CPC .............. A61F 5/0195; A61F 5/0585; A61F 2005/0174; A61F 2005/001; A61F 2005/0197
USPC ......... 602/60, 61, 62, 63, 65, 66, 27, 28, 29
See application file for complete search history.

(56) References Cited

U.S. PATENT DOCUMENTS

| | | | |
|---|---|---|---|
| 4,459,980 | A | 7/1984 | Perser et al. |
| 5,584,072 | A | 12/1996 | Kim et al. |
| 6,146,350 | A * | 11/2000 | Morton ................ A61F 5/0127 602/5 |
| 6,767,332 | B1 | 7/2004 | Pardue et al. |
| 6,887,213 | B2 | 5/2005 | Smits |
| 6,945,947 | B2 | 9/2005 | Ingimundarson et al. |
| 7,766,851 | B2 | 8/2010 | Lindh et al. |
| 8,465,445 | B2 | 6/2013 | George |
| 10,729,574 | B2 * | 8/2020 | Johnsson .............. A61F 5/0111 |
| 2004/0134500 | A1 * | 7/2004 | Ingimundarson ..... A61F 5/0113 128/882 |
| 2007/0038169 | A1 * | 2/2007 | Alon .................... A61F 5/0111 602/27 |
| 2009/0037001 | A1 | 2/2009 | Lindh et al. |
| 2009/0105624 | A1 * | 4/2009 | Warner ................ A61F 5/0111 602/27 |
| 2009/0198166 | A1 * | 8/2009 | Shlomovitz ........... A61F 5/0111 602/28 |
| 2011/0105969 | A1 | 5/2011 | Nace |
| 2011/0105973 | A1 | 5/2011 | Watts |
| 2011/0196277 | A1 * | 8/2011 | Savard .................. A61F 5/0127 602/28 |
| 2011/0306911 | A1 | 12/2011 | Tran |
| 2014/0257162 | A1 | 9/2014 | Falkenman et al. |

FOREIGN PATENT DOCUMENTS

| | | |
|---|---|---|
| CN | 202198708 U | 4/2012 |
| DE | 202004009893 U1 | 8/2004 |
| DE | 10338129 A1 | 3/2005 |
| DE | 29924933 U1 | 12/2006 |
| DE | 60315698 T2 | 6/2008 |
| RU | 2092136 C1 | 10/1997 |
| RU | 061549 U1 | 3/2007 |
| WO | 01/34071 A1 | 5/2001 |
| WO | 2007/106017 A1 | 9/2007 |

* cited by examiner

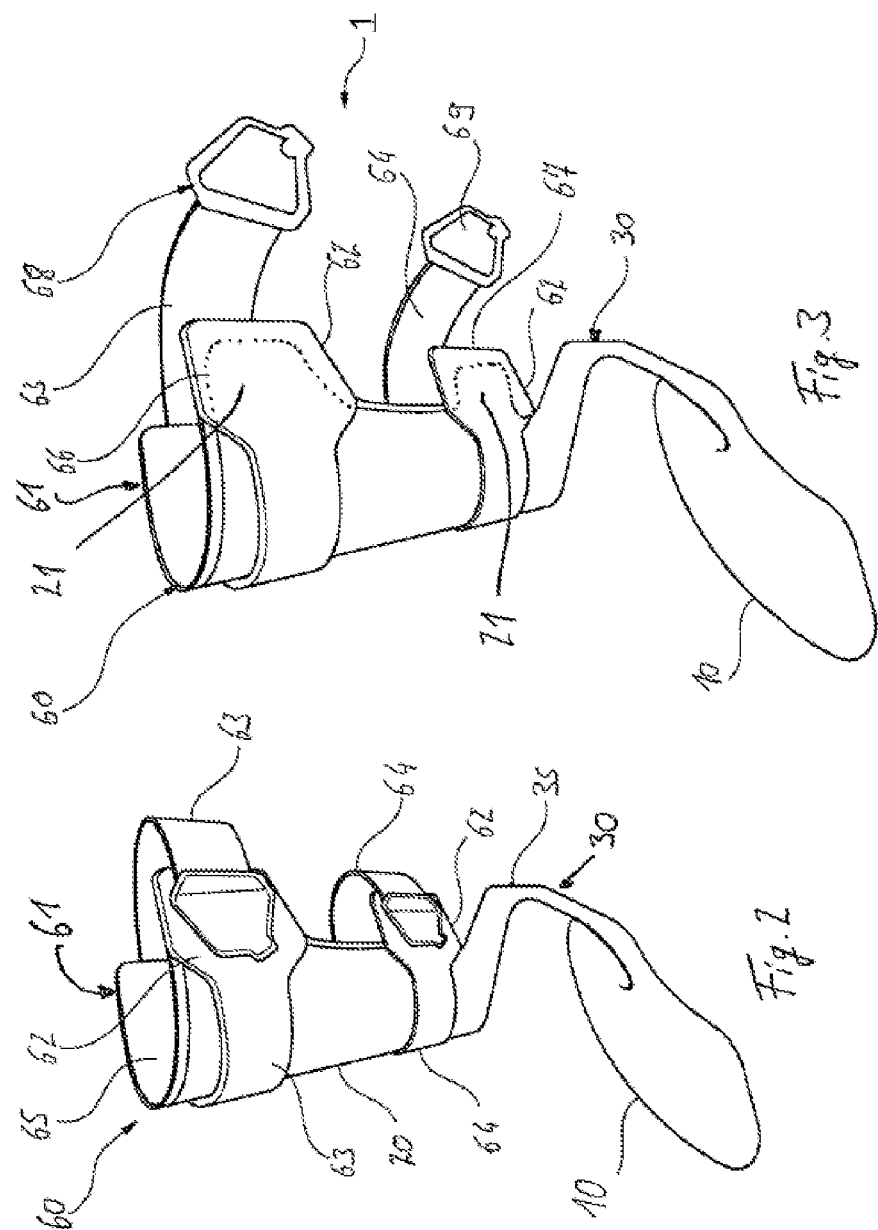

ANKLE/FOOT ORTHOSIS

CROSS-REFERENCE TO RELATED APPLICATIONS

This is a continuation application of U.S. patent application Ser. No. 18/074,258, filed 2 Dec. 2022, which is a continuation application of U.S. patent application Ser. No. 16/926,595, filed 10 Jul. 2020, now U.S. Pat. No. 11,517,463, and entitled ANKLE/FOOT ORTHOSIS, which is a continuation application of U.S. patent application Ser. No. 14/406,835, filed 10 Dec. 2014, now U.S. Pat. No. 10,729,574, and entitled ANKLE/FOOT ORTHOSIS, which is a U.S. National Entry Application from PCT International Patent Application No. PCT/EP2013/001663, filed 6 Jun. 2013, and entitled ANKLE/FOOT ORTHOSIS, which claims the benefit of German Patent Application No. 102012011466.4, filed 12 Jun. 2012, the disclosures of which are incorporated, in their entireties, by this reference.

TECHNICAL FIELD

The invention relates to an ankle/foot orthosis with a foot part, which has a sole for receiving a foot, and with a shin part which, when fitted in place, bears on the frontal aspect of a shin and is connected to the foot part via a spring.

BACKGROUND

If the ankle joint lacks stability and the muscle strength is inadequate, it may be useful and necessary to use an ankle/foot orthosis. The ankle/foot orthosis keeps the foot in a relationship to the shin and prevents unwanted dorsal flexion, and also plantar flexion when the foot is unloaded. During walking, the orthosis assists the patient by maintaining a dorsally flexed position at heel strike and by allowing pushing-off in the terminal stance phase. Unwanted pronation and supination of the foot are likewise avoided.

DE 603 15 698 T2 relates to an ankle/foot orthosis with a structural frame which has a foot plate, an inner part and an ankle part and which splits into two frontal support elements, which are arranged medially and laterally on the frontal aspect of the shin. The ankle/foot orthosis can be fitted on the patient using a fastening device in the form of a velcro fastener.

SUMMARY

The object of the present invention is to make available an ankle/foot orthosis which permits a high level of functionality, allows simple insertion into the shoe and is easy to fit on the patient.

According to the invention, this object is achieved by an ankle/foot orthosis having the features of the main claim. Advantageous embodiments and developments of the invention are disclosed in the dependent claims, in the description, and in the figures.

In the ankle/foot orthosis according to the invention, with a foot part, which has a sole for receiving a foot, and with a shin part which, when fitted in place, bears on the frontal aspect of a shin and is connected to the foot part via a spring, provision is made that the spring, behind an ankle area, forms a hinge area that allows a movement of the shin part relative to the foot part in the anterior-posterior direction. The course of the spring behind an ankle area, i.e., the area where the natural axis of the ankle joint lies, ensures that no spring material presses against the ankle or the shin.

In a development of the invention, provision is made that the spring is arranged extending medially. The medial course of the spring prevents the spring from catching on objects during walking, in addition to which the medial course of the spring ensures an unobtrusive positioning of the ankle/foot orthosis.

Moreover, the spring can in this way be connected to the foot part in the area of the plantar arch, as a result of which the course of the spring in the transition area can be more flowing than in the lateral sole area.

The hinge area of the spring is designed to be torsionally stable about an axis that runs from proximal to distal, i.e., corresponds substantially to a vertical direction. It is thus possible that the orientation of the foot relative to the shin is maintained during walking and there is only a spring movement, on account of the hinge area, in the sagittal plane, i.e., about an axis extending transversely with respect to the direction of walking.

The hinge area is advantageously designed to be flexurally stiff in the medial-lateral direction, in order to counteract a pronation movement or supination movement of the foot or of the foot part.

In one embodiment of the invention, provision is made that the spring extends medially inward from the foot part and obliquely upward in the dorsal direction, such that it protrudes behind the ankle area. From the ankle area, it then extends obliquely upward in the ventral direction. The course of the spring is therefore such that a lower spring portion extends obliquely rearward at an articulation of the spring in the area of the plantar arch, wherein the front edge of the spring lies behind the axis of the joint. From the farthest posterior position of the spring, an upper portion of the spring then extends obliquely forward in order to support the shin.

To form the hinge area, provision is made that the spring has a tapering in the anterior-posterior direction, such that, on account of the narrowed configuration of the spring in the area with reduced material, a defined zone is provided that facilitates yielding in the anterior-posterior direction.

In order to make dorsal flexion and plantar flexion easier, the spring can have a lower section modulus in the anterior-posterior direction than in the medial-lateral direction. This lower section modulus can be achieved by a specific geometric configuration of the spring; different section moduli in the respective orientations can be provided in particular in the hinge area.

To permit pivoting in the anterior-posterior direction and at the same time to avoid pivoting in the medial-lateral direction, so that the foot remains on the foot part in the adopted orientation, provision can also be made that the spring has, in the hinge area, a material structure that has a greater elasticity in the anterior-posterior direction than in the medial-lateral direction. This can be achieved, for example, by a specific choice of fiber-reinforced materials for the spring. For example, carbon can be used as fiber material in the medial-lateral direction, carbon having less elasticity than, for example, glass fiber, aramid fiber or polyethylene fiber, which are responsible for the stiffness or elasticity in the anterior-posterior direction. The different elasticities can therefore be achieved not only by geometric variations but also by the suitable orientations of the fiber reinforcements within the spring.

The shin part can have a gutter shape or cup shape and is flexurally stiff in the medial plane, such that a stable contact of the shin on the shin part is permitted. By virtue of the flexurally stiff configuration in the medial plane, it is possible to achieve a good transfer of force from the foot part to the shin part via the spring, without this leading to punctiform loads in the shin area.

The spring can be curved in the medial direction with respect to a sagittal plane, in order to extend medially inward from the foot part, so as not to touch the ankle protruding medially to the contralateral side but instead to run around it both medially and also in the posterior direction.

The shin part can have a padding to make the orthosis easier to wear. The padding can be secured on the shin part via pockets on projections. It is likewise possible that the pockets bear medially and laterally on the entire shin part, such that the shin part is received, at least at the edges, completely in the pockets. To secure the orthosis to the leg and also the padding to the shin part, fastening elements can be provided which are guided from the lateral side to the medial side in order to make fitting and securing easier. The spring can be designed as an arc and, as a separate component, can be connected to a separate foot part and a separate shin part. It is also possible in principle that the ankle/foot orthosis is in one piece, such that the spring is an integral component both of the foot part and also of the shin part. The spring itself can be designed as a separate part and can be connected to the respective adjoining components via plug connections, if appropriate by form-fit securing, or an adhesive connection.

Furthermore, provision can be made that the spring in the ankle area has the least stiffness against bending about an ankle joint axis, thereby permitting mobility in the anterior-posterior direction. During walking or standing, the point of introduction of force into the foot or into the foot part changes according to the phase of movement or the shifting of weight. The forces acting on the ankle joint cause moments about the respective joint axis, wherein, at a constant force, the active moment increases with the distance from the joint axis. On account of the geometric relationships, the greatest moment is therefore applied around the axis of the ankle joint, since the point of introduction of force is at a maximum distance from the axis of the ankle joint or the hinge area, whereas, on account of the geometric conditions, only a small moment is applied to the ankle area, and therefore also to the hinge area, about the longitudinal axis of the foot. This results in a relative stiff configuration against a supination movement or pronation movement, since, on account of the short distance from the hinge area, a smaller moment is active, whereas a relatively soft and elastic configuration is present for a plantar flexion and dorsal flexion, since greater yielding is afforded on account of the greater active moment around the hinge area.

BRIEF DESCRIPTION OF THE DRAWINGS

Illustrative embodiments of the invention are explained in more detail below with reference to the attached figures, in which:

FIG. 2 shows an ankle/foot orthosis with padding;
and
FIG. 3 shows an ankle/foot orthosis with open fastening elements.

FIG. 1 shows an ankle/foot orthosis in a schematic view, with a foot part 10 and a shin part 20, which are connected to each other via a spring. The foot part 10 has a sole 11 on which it is possible to position a foot indicated by the broken line. In the metatarsal region, elevations are provided medially and laterally on the sole 11, in order to support the foot both in the medial and also in the lateral direction. The elevations 12 can also enclose the heel. The foot part 10 is advantageously in one piece and is made of a dimensionally stable, slightly elastic material, which allows it to perform a heel-to-toe movement of the foot during walking. The stability is chosen such that sufficient support of the foot is ensured.

Figure 1:
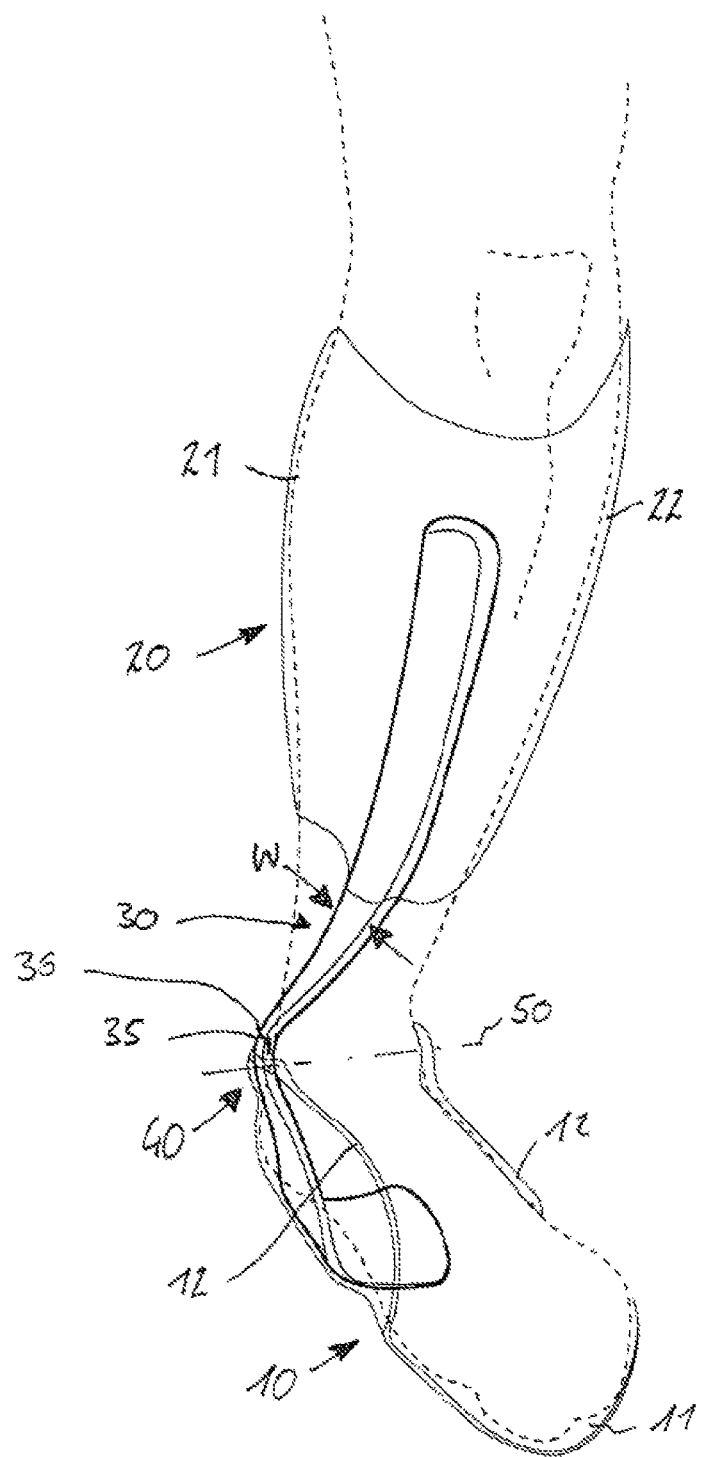
FIG. 1 shows an ankle/foot orthosis in a schematic set-up.

The shin part 20 has a cup shape or gutter shape and follows the shape of the natural leg. The shin part 20 can be flexurally stiff in the medial plane, such that there is firm contact along the longitudinal extent of the shin. In order to permit variations in volume during wear or also to permit adaptation to different users, the shin part 20 can be elastic in the medial and/or lateral direction at its end areas, such that the gutter-shaped shin part 20 can widen or, by suitable fastening elements, can be moved toward the lower leg. It is likewise possible that the shin part 20 is elastic only in one direction, i.e., either medially or laterally, since it is sometimes advantageous for one contact to be stiff while the other contact yields elastically. For example, if the medial contact is stiff, a rotary movement of the leg can be prevented.

Both components, i.e., the shin part 20 and also the foot part 10, can be produced from fiber-reinforced plastics and are advantageously made in one piece. In an alternative embodiment, a multi-part configuration both of the foot part 10 and also of the shin part 20 is possible.

In the illustrative embodiment shown, the foot part 10 is connected to the shin part 20 via a medially arranged spring 30. Foot part 10, shin part 20 and spring 30 are designed as separate components and fastened to one another, for example via a plug connection, which is subsequently fixed, for example by a form-fit element or an adhesive bond. Alternatively, the foot part 10, the shin part 20 and the spring 30 are permanently interconnected, for example adhesively bonded, welded, baked or laminated onto to one another. It is also possible in principle to produce both the foot part 10 and also the spring 30 and the shin part 20 in one piece from fiber-reinforced plastics or another material.

The spring 30 extends medially from the underside of the sole 11 of the foot part 10 and proximally across the plantar arch in the direction of the natural ankle, wherein the course from the sole 11 to an ankle area 40 runs obliquely in the posterior and proximal direction, i.e., obliquely rearward and upward, wherein the front edge of the spring 30 runs to a position behind the axis 50 of the natural ankle joint. From there, the spring 30 runs obliquely in the anterior and proximal direction, i.e., obliquely forward and upward, until it extends proximally, i.e., upward, substantially parallel to the shin. The shin part 20 is fastened to the proximal, upper end of the spring 30.

In the ankle area 40 of the ankle/foot orthosis, the spring 30 forms a hinge area 35, which lies approximately at the height of the axis 50 of the ankle joint. In this hinge area 35, a flexion of the spring 30 is permitted substantially about the axis 50 of the natural joint, such that the shin part 20 can be moved elastically relative to the foot part 10. To form the hinge area 35, provision is made that the cross section changes from distal to proximal along the course of the spring 30 and has, in the hinge area 35, the lowest section modulus against a movement in the anterior-posterior direction, i.e., in the sagittal plane. For this purpose, the spring 30 in the hinge area 35 is provided, approximately at the height of the axis 50 of the natural ankle joint, with a tapering 36, such that the lowest section modulus is present in this area. The thickness of the spring 30, i.e., the extent in the medial-lateral direction, can be made substantially constant.

From the sole 11, the spring 30 firstly extends medially inward, in order then to extend in an arc in the lateral direction behind the ankle. After the hinge area 35, the spring 30 extends laterally in an arc shape until it merges into the shin part 30. The spring 30 thus extends in two arcs, wherein the greatest medial curvature lies below the hinge area 35 or in the hinge area 35, while the maximum posterior curvature lies behind the ankle area 40 of the ankle joint.

FIG. 2 shows a variant of the ankle/foot orthosis, with a shin part 20, a fastening means 60, and a foot part 10, which is connected to the shin part 20 via the spring 30. The spring 30 in this case permits only a slight, defined movement of the shin part 20 relative to the foot part 10. The foot part 10 is designed as a flat sole plate, which substantially follows the outer contour of a foot or of a shoe. The illustrative embodiment shown is in one piece and made from a fiber-reinforced plastic.

In the fitted state, the shin part 20 bears on the shin of the orthosis user and at least partially encloses the shin medially and laterally. The contour of the shin part 20 is substantially gutter-shaped or cup-shaped and can have recesses or apertures to permit improved ventilation of the shin area. A fastening means 60 is arranged on the inner side of the shin part 20 facing toward the orthosis user in the fitted state, said fastening means 60 at the same time being provided with a padding 65, such that the hard, cup-like structure of the shin part 20 does not lie directly on the lower leg.

Receiving regions 21 in the form of projections or tongues, which are shown in FIG. 3, are arranged both medially and also laterally on the shin part 20. The receiving regions 21 or projections are formed at the proximal end and distal end of the shin part 20 and, when the orthosis is in the fitted state on the orthosis user, face toward the rear. The receiving regions 21 are referred to below as projections, which term is also meant to include a configuration in which structures adjoining the shin part 20 are suitable for being received in pockets in order to bring about a form-fit securing of the padding 65.

On the fastening means 60, pockets 61, 62 are formed into which the projections or receiving regions 21 are pushed. By pushing the projections or receiving regions 21 into the pockets 61, 62, the fastening means 60 is secured on the shin part 20. Provision is made here that the lateral pockets 61 are deeper than the medial pockets 62, and provision is likewise made that the lateral projections or receiving regions 21 are longer than the medial projections or receiving regions 21, wherein the depth of the pockets 61, 62 corresponds to the lengths of the projections 21. The illustrative embodiment provides two pockets 61, 62 and two projections 21 on the medial and lateral sides, respectively, which are offset relative to each other in the longitudinal extent, such that two proximal and two distal pairs of pockets 61, 62 and projections or receiving regions 21 result. Alternatively, it is also possible for just one pocket to be provided medially and laterally and to be secured on a corresponding receiving region 21.

Fastening elements 63, 64 are provided on the fastening means 60, both at the proximal edge and also at the distal edge of the shin part 20, via which fastening elements 63, 64 the orthosis is secured on the limb. The fastening elements 63, 64, in the form of straps or bands, are secured, for example welded, adhesively bonded or sewn, on the medial side on the fastening means 60 to form the medial pockets 62. From the medial pocket 22, the connection element 63, 64 designed as a strap is guided externally along the outer side of the shin part 20 and is secured externally on the lateral pocket 61, for example by a velcro fastener. In the case of an elastic configuration of the strap-like fastening element 63, 64, the medial and lateral pockets 61, 62 are pretensioned toward each other in the circumferential direction, such that the forwardly open pockets 61, 62 cannot slide down from the rearwardly pointing projections 21. To further secure the orthosis, the respective connection element 63, 64 is then guided rearward around the limb (not shown) from the lateral side to the medial side and is secured there on a fixing means 66, 67. The connection element 63, 64 is thus guided once around the orthosis and the limb, wherein the free end is secured on the outer side of the medial pocket 62. At the free end of the fastening element 63, 64, locking elements 68, 69 are secured, for example in the form of detachable velcro elements, which can be secured on the outer side of the fastening element 63, 64 or on fleeced areas of the fixing means 66, 67 externally on the medial pockets 62. The securing on the fastening elements 63, 64 and on the fixing means 66, 67 is reversible. The fastening elements 63, 64 can be flexible and nonelastic, flexible and elastic, or elastic only in parts, and it is likewise possible that the connection element 63, 64 is secured reversibly on the fastening means 60, for example by velcro fasteners.

In the fitted state as shown in FIG. 2, the connection element 63, 64 bridges the gap in the cup-like shin part 20 from lateral to medial. The shin part 20 can permit a deformation of the projections 21 toward each other, such that an adjustment to the dimensions of the limb on which the orthosis is to be fitted can take place. The adjustment can be made via the circumferential force applied by the fastening elements 63, 64.

The embodiment shown is especially advantageous for patients who are paralyzed on one side or weakened on one side. When the connection element 63 is guided from the medial side to the lateral side, stretched and secured with tensioning on a lateral pocket 61, the hand that is unaffected by the weakness can be used to safely secure the orthosis by then guiding the connection element 63, 64 behind the limb and locking it on the medial side.

The fastening means 60 can also be designed as a one-part element or as a multi-part, permanently interconnected element that has a cushioning function. The medial and lateral projections 21 form self-adaptive side wings which adapt automatically to the shape of the limb under the circumferential force that is applied by the connection element 63, 64.

With Y-shaped velcro tapes 68, 69 as hook areas, it is possible to easily shorten the fastening elements 63, 64 designed as straps, by removing the Y-shaped Velcro tapes from the fleeced fastening elements 63, 64, shortening them to the desired length and then reapplying them.

Particularly in the case of stroke patients, it must be noted that they are able to fit the orthosis using only the unaffected side of the body. By virtue of the fastening elements 63, 64 being arranged laterally and being guided from lateral to medial in order to secure the orthosis, it is possible for the orthosis user, in a seated position, to grasp the connection element 63, 64 laterally, using his or her unaffected side, and to simply pull it in the medial direction and secure it there on the hook and loop areas 66, 67 provided there.

The invention claimed is:

1. An ankle/foot orthosis, comprising:
a foot part, which has a sole configured to receive a foot;
a shin part having an elongate gutter shape or cup shape that is configured to extend along a length of a shin, the shin part being configured to extend along and bear on a frontal aspect of the shin and being connected to the foot part via a spring;
the spring further comprising a first arc and a second arc, the first arc being configured to extend medially from the foot part and to extend in an arc behind an ankle in a lateral direction to form a hinge area, and wherein the second arc is configured to curve laterally and anteriorly from the hinge area to merge into the shin part, wherein the first arc has a larger medial bulge than the second arc and the hinge area forms a furthest posterior position of the spring.

2. The ankle/foot orthosis of claim 1, wherein the spring and the shin part are made in one piece.

3. The ankle/foot orthosis of claim 1, wherein the spring and the shin part are separate components and fastened to each other, and wherein the shin part is fastened to the spring at a proximal end of the shin part.

4. The ankle/foot orthosis of claim 1, wherein the spring is configured to extend proximally substantially parallel to the shin.

5. The ankle/foot orthosis of claim 1, wherein the spring and the foot part are made in one piece from a fiber-reinforced plastic.

6. The ankle/foot orthosis of claim 1, wherein foot part, the shin part, and the spring are permanently connected, bonded or laminated together.

7. The ankle/foot orthosis of claim 1, wherein the hinge area is designed to be torsionally stable about a proximal-distal axis.

8. The ankle/foot orthosis of claim 1, wherein the hinge area is designed to be flexurally stiff in a medial-lateral direction.

9. The ankle/foot orthosis of claim 1, wherein the spring has a width measured in an anterior-posterior direction that tapers from the foot part in a posterior and proximal direction such that a smallest width measured in the anterior-posterior direction is along a portion of the spring.

10. The ankle/foot orthosis of claim 1, wherein the shin part has a greater length in a longitudinal dimension than a width in a medial/lateral direction.

11. The ankle/foot orthosis of claim 1, wherein the shin part is flexurally stiff in a medial plane.

12. The ankle/foot orthosis of claim 1, wherein the spring is connected to the foot part medially in the area of an arch of the foot part.

13. The ankle/foot orthosis of claim 1, wherein the first arc extends medially from the foot part and is configured to extend diagonally upwards dorsally behind the ankle.

14. The ankle/foot orthosis of claim 1, wherein the second arc extends from the hinge area obliquely forwards.

15. The ankle/foot orthosis of claim 1, wherein the spring, the shin part, and the foot part are made in one piece.

16. The ankle/foot orthosis of claim 1, wherein the foot part is formed as a single piece of a dimensionally stable, elastic material, allowing it to perform a heel-to-toe movement of the foot part during walking.

17. The ankle/foot orthosis of claim 1, wherein the shin part is configured to be flexurally stiff in a medial plane such that the shin part firmly contacts the shin along a longitudinal extent of the shin.

18. The ankle/foot orthosis of claim 1, wherein the shin part is configured to be elastic in the medial and/or lateral direction at an end area of the shin part.

19. The ankle/foot orthosis of claim 1, wherein the first arc is configured to extend from the foot part to the ankle at an angle in a posterior and proximal direction, and wherein a front edge of the spring is configured to extend behind a natural ankle joint axis, and wherein the second arc is configured to extend obliquely in an anterior and proximal direction until the second arc extends parallel to a tibia proximally.

20. The ankle/foot orthosis of claim 1, wherein the foot part comprises a flat sole plate that follows an outer contour of the foot or of a shoe.

21. An ankle/foot orthosis, comprising:
a foot part, which has a sole configured to receive a foot; and
a shin part having an elongate gutter shape or cup shape that is configured to extend along a length of a shin, the shin part being further configured to bear on a frontal aspect of the shin, the shin part being connected to the foot part via a spring;
wherein the spring comprises a first arc and a second arc, the first arc being configured to extend medially from the foot part in an arc behind an ankle in a lateral direction to form a hinge area, and the second arc being configured to curve laterally and anteriorly from the hinge area to merge into the shin part, wherein the first arc has a larger medial bulge than the second arc and the hinge area forms a furthest posterior position of the spring, and wherein the foot part, the shin part, and the spring are integrally formed together.

\* \* \* \* \*

UNITED STATES PATENT AND TRADEMARK OFFICE
CERTIFICATE OF CORRECTION

| | | |
|---|---|---|
| PATENT NO. | : 12,324,762 B2 | Page 1 of 1 |
| APPLICATION NO. | : 18/539596 | |
| DATED | : June 10, 2025 | |
| INVENTOR(S) | : Jan Johnsson et al. | |

It is certified that error appears in the above-identified patent and that said Letters Patent is hereby corrected as shown below:

On the Title Page

At item (72) Inventors:

Delete "Markus TUTTEMANN, Duderstadt (DE)"
Insert --Markus TUTTEMANN, Waltrop (DE)--

Delete "Boris LJUBIMIR, Waltrop (DE)"
Insert --Boris LJUBIMIR, Korntal-Munchingen (DE)--

Delete "Norbert SCHIMEK, Duderstad (DE)"
Insert --Norbert SCHIMEK, Kirchworbis (DE)--

Delete "Wolfgang KEINER, Kirchworbis (DE)"
Insert --Wolfgang KEINER, Duderstadt (DE)--

Signed and Sealed this
Sixteenth Day of September, 2025

Coke Morgan Stewart
*Acting Director of the United States Patent and Trademark Office*